United States Patent [19]
Jenkins et al.

[11] Patent Number: 5,919,467
[45] Date of Patent: Jul. 6, 1999

[54] POWDER COSMETIC COMPOSITIONS

[75] Inventors: Delyth Myfanwy Jenkins, Egham, United Kingdom; Gillian Scott Briggs, Cockeysville, Md.; Karen Fish, Bracknell, United Kingdom

[73] Assignee: The Proctor & Gamble Company, Cincinnati, Ohio

[21] Appl. No.: 08/704,700

[22] PCT Filed: Feb. 27, 1995

[86] PCT No.: PCT/US95/02445

§ 371 Date: Oct. 29, 1996

§ 102(e) Date: Oct. 29, 1996

[87] PCT Pub. No.: WO95/25503

PCT Pub. Date: Sep. 28, 1995

[30] Foreign Application Priority Data

Mar. 18, 1994 [GB] United Kingdom ................... 9405320

[51] Int. Cl.$^6$ ..................................... A61K 7/48
[52] U.S. Cl. ......................... 424/401; 424/69; 424/78.02
[58] Field of Search ............................... 424/489, 64, 69, 424/63, 401, 78.02, 65, 70.1; 514/844

[56] References Cited

U.S. PATENT DOCUMENTS

| | | | |
|---|---|---|---|
| 4,379,136 | 4/1983 | Mochida | 424/65 |
| 4,465,866 | 8/1984 | Takaishi et al. | 568/618 |
| 4,804,532 | 2/1989 | Busch, Jr. | 424/69 |
| 4,873,078 | 10/1989 | Edmundson et al. | 424/64 |
| 4,980,157 | 12/1990 | Mercado et al. | 424/69 |
| 5,089,256 | 2/1992 | Scheller et al. | 424/63 |
| 5,122,418 | 6/1992 | Nakane et al. | 424/401 |
| 5,162,378 | 11/1992 | Guthauser | 514/785 |
| 5,188,831 | 2/1993 | Nicoll et al. | 424/401 |
| 5,356,627 | 10/1994 | Da Cunha et al. | 424/401 |
| 5,482,710 | 1/1996 | Slavtcheff et al. | 424/195.1 |
| 5,484,597 | 1/1996 | Slavtcheff et al. | 424/401 |
| 5,549,888 | 8/1996 | Venkateswaran | 424/78.02 |

FOREIGN PATENT DOCUMENTS 1032-902 5/1989 China ........................... A61K 07/02

*Primary Examiner*—Jyothsna Venkat
*Attorney, Agent, or Firm*—Loretta J. Henderson; George W. Allen; David L. Suter

[57] ABSTRACT

Cosmetic composition in the form of a powder comprising branched chain aliphatic hydrocarbon having a weight average molecular weight of from about 100 to about 15,000 and the remainder of the composition comprising one or more cosmetic powder base components selected from pigments, matte finishing agents, fillers and binders, and mixtures thereof. The compositions provide improved adhesion to the skin, increased wear, coverage and reduced rub-off.

13 Claims, No Drawings

POWDER COSMETIC COMPOSITIONS

TECHNICAL FIELD

The present invention relates to powder cosmetic compositions. In particular, it relates to powder cosmetic compositions for purposes of make-up and the like which provide improved adhesion to the skin, increased wear, coverage and reduced rub-off.

BACKGROUND OF THE INVENTION

Make-up compositions are generally available in the form of liquid or cream suspensions, emulsions, gels, anhydrous oil and wax compositions or pressed and loose powders.

Make-up is normally applied to the face in two stages. In a first stage, a liquid or cream foundation is applied. This is followed by application of a powder composition, the function of which is to impart a smooth finish to facial skin, masking minor visible imperfections and shine.

W088/00039 discloses a pressed facial cosmetic powder comprising a blend of moisturising and oil absorbing clays, filler, dry binder and liquid binder.

U.S. Pat. No. 4,804,532 recites a facial cosmetic powder which utilises crystalline silica in much lower concentration than that employed in the then prior art compositions. This powder, used as a blush or a facial coating, is said to be effective in hiding skin wrinkles, lines and pores. The composition is a mixture of a colour phase and a diluent phase. The colour phase is formed by blending crystalline silica with colourants. The resultant colour phase is mixed with the diluent phase, essentially formed from nacreous materials such as talc and mica, to form the composition.

Pressed and loose cosmetic powder compositions for application to the face are well-known and help to provide good skin coverage and appearance with reduced shine, especially when used with foundations. It would however be desirable to improve the substantivity characteristics such as improved skin adhesion, wear and coverage of cosmetic powder compositions. It would also be desirable to provide a powder composition having prolonged topical anti-acne and/or anti-bacterial activity. There are many compounds which are known to exhibit anti-acne and/or anti-bacterial properties when applied topically to the skin. A commonly used keratolytic agent having anti-acne activity is salicylic acid. Zinc oxide is also known for use in anti-acne compositions.

CN-A-1032902 discloses a skin disease treatment and protection powder containing borax, zinc oxide, benzoic acid, talcum powder and salicylic acid.

It is accordingly a primary object of this invention to provide a powder cosmetic composition having improved skin adhesion, wear and coverage and reduced rub-off. It is also an object of the present invention to provide a powder cosmetic composition having anti-acne activity over extended periods of time.

SUMMARY OF THE INVENTION

According to the present invention there is provided a cosmetic composition in the form of a powder comprising:

(a) from about 0.01% to about 20% by weight of silicone or mixture of silicones, the silicone or silicone mixture comprising an alkylmethylsiloxane polymer having the formula:

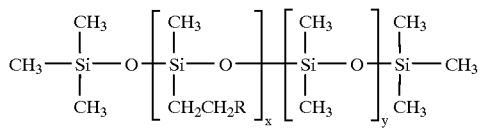

wherein x has a value of from 1 to about 1,000, y has a value of from 0 to 1,000 and R is selected from H and $C_1$–$C_{50}$ alkyl; and (b) the remainder comprising one or more cosmetic powder base components selected from pigments, matte finishing agents, fillers and binders, and mixtures thereof.

The powder cosmetic compositions of the present invention provide improved adhesion to the skin, coverage and wear characteristics. Highly preferred embodiments also provide excellent anti-acne activity. According to another aspect of the present invention there is provided a cosmetic composition in the form of a powder comprising;

(a) from about 0.1% to about 20% by weight of branched chain aliphatic hydrocarbon having a weight average molecular weight of from about 100 to about 15,000; and (b) the remainder of the composition comprising one or more cosmetic powder base components selected from pigments, matte finishing agents, fillers and binders and mixtures thereof.

All levels and ratios are by weight of total composition, unless otherwise indicated. Chain length, degrees of alkoxylation and molecular weights are also specified on a weight average basis.

DETAILED DESCRIPTION OF THE INVENTION

The powder cosmetic composition according to one aspect of the present invention comprises a silicone or mixture of silicones together with one or more cosmetic base powder components inclusive of pigments, fillers and binders. According to this first aspect of the present invention a first essential component is a silicone or mixture of silicones. The silicone or mixture of silicones used herein comprises an alkylmethylsiloxane polymer having the formula:

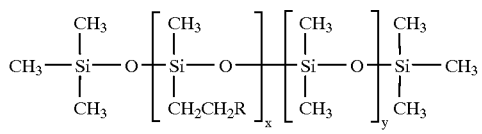

wherein x has a value of from about 1 to about 1000, y has a value of from 0 to about 1000 and R is selected from H and $C_1$–$C_{50}$ alkyl. In preferred embodiments R is more preferably a $C_4$–$C_{24}$ alkyl group.

Suitable alkylmethylsiloxanes for use herein are commercially available from Dow Corning Corporation. Particularly preferred for use in the powder compositions of the present invention is Dow Corning 2502 cosmetic fluid which is known by its CTFA designation as Cetyl Dimethicone.

The silicone or mixture of silicones is present in the compositions of the invention at a level of from about 0.01% to about 20%, preferably from about 0.5% to about 10% by weight of composition. Also suitable for use herein are mixtures of alkylmethylsiloxanes with one or more silicone materials as set out below.

The powder compositions according to the invention preferably also comprise a branched chain aliphatic hydrocarbon having a molecular weight of from about 100 to about 15,000, preferably from about 200 to about 1000. The branched chain aliphatic hydrocarbon is preferred herein from the viewpoint of providing improved skin adhesion and can be used either alone or in combination with the above mentioned silicone or mixture of silicones.

The branched chain aliphatic hydrocarbon can be selected from isododecane, isohexadecane, isoeicosane, isooctahexacontane, isohexapentacontahectane and isopentacontaoctactane, and mixtures thereof. Suitable for use herein are branched chain aliphatic hydrocarbons sold under the trade name Permethyl (RTM) and commercially available from Presperse Inc., P.O. Box 735, South Plainfield, N.J. 07080, U.S.A. Particularly suitable herein from the viewpoint of improved skin adhesion, coverage, wear and reduced rub-off is Permethyl 102A which is chemically known as isoeicosane.

The compositions herein also comprise one or more cosmetic base powder components selected from pigments, fillers and binders, and mixtures thereof. It will be appreciated that many of the conventional components of powder cosmetic compositions have more than one functionality and they can therefore be classified under more than one functional type, e.g. $TiO_2$, talc and zinc oxide all act both as pigments and fillers. Zinic oxide is also particularly useful herein as an anti-acne component. Polyethylene can act both as matte finishing agent and binder. In total, these other cosmetic base powder components will generally comprise up to about 99% by weight, preferably from about 60% to about 98% by weight of the composition.

Suitable pigments for use herein can be inorganic and/or organic. Also included within the term pigment are materials having a low colour or lustre such as matte finishing agents, and also light scattering agents. Examples of suitable pigments are iron oxides, acylglutamate iron oxides, ultramarine blue, D&C dyes, carmine, and mixtures thereof.

The powder compositions can also include at least one matte finishing agent. The function of the matte finishing agent is to hide skin defects and reduce shine. Such cosmetically acceptable inorganic agents, i.e., those included in the CTFA Cosmetic Ingredient Dictionary, Third Ed., as silica, hydrated silica, silicone-treated silica beads, mica, talc, polyethylene, calcium silicate, titanium dioxide, bentonite, hectorite, kaolin, chalk, diatomaceous earth, attapugite, zinc oxide and the like may be utilised. Of particular usefulness as a matte finishing agent is low lustre pigment such as titanated mica (mica coated with titanium dioxide) coated with barium sulphate. Of the inorganic components useful as a matte finishing agent, low lustre pigment, talc, hydrated silica, kaolin, titanium dioxide and mixtures thereof are particularly preferred. Materials suitable for use herein as light-scattering agents can be generally described as spherical shaped inorganic materials having a particle size of up to about 100 microns, preferably from about 5 to about 50 microns, for example spherical silica particles.

The total concentration of high lustre colouring agents in the powder cosmetic compositions may be from about 0.01% to about 30% by weight, preferably from about 1% to about 20%, and more preferably from about 1% to about 15% by weight of the total composition, the exact concentration being dependent to some extent upon the specific mixture of pigments selected to achieve the desired shades. The preferred compositions contain from about 0.1% to about 5% by weight of iron oxides.

Also suitable for use herein especially from the viewpoint of moisturisation, skin feel, skin appearance and emulsion compatibility are treated pigments. Pigments can be treated with compounds such as amino acids (e.g., lysine), silicones, lauroyl, collagen, polyethylene, lecithin and ester oils. The more preferred pigments are the silicone (polysiloxane) treated pigments.

The powder compositions herein can also comprise one or more filler materials. Examples of suitable fillers include talc, rice starch and/or bismuth oxychloride, preferably talc.

It may also be desirable to include a dry binder in the powder compositions of the invention. Examples of suitable dry binders include magnesium stearate, zinc stearate, calcium stearate, lithium stearate, and mixtures thereof.

There is preferably also included in the compositions of the present invention an anti-acne active. Suitable anti-acne actives for use herein include salicylic acid, retinoic acid, azelaic acid, lactic acid, glycolic acid, pyruvic acid, flavonoids, and derivatives and mixtures thereof. The anti-acne active used herein is preferably salicylic acid. The anti-acne active is present at a level of from about 0.01% to about 10% by weight of composition.

Another highly preferred component in the compositions herein is an anti-bacterial agent. The preferred anti-bacterial agent for use herein is zinc oxide. Especially preferred is ultrafine zinc oxide having an average particle size of from about 0.1 $\mu$m to about 5 $\mu$m, preferred from about 0.5 to about 1.5 $\mu$m. The compositions herein based on a mixture of zinc oxide with silicone and/or branched chain hydrocarbon are found to be especially effective against bacteria of the P. acnes variety and therefore have excellent anti-acne activity.

The powder compositions of the present invention can also comprise a particulate cross-linked hydrophobic acrylate or methacrylate copolymer. This copolymer is particularly valuable for reducing shine and controlling oil. The cross-linked hydrophobic polymer is preferably in the form of a copolymer lattice and can contain at least one active ingredient dispersed uniformly throughout and entrapped within the copolymer lattice. Alternatively, the hydrophobic polymer can take the form of a porous particle having a surface area ($N_2$-BET) in the range from about 50 to 500, preferably 100 to 300 $m^2/g$ and having the active ingredient absorbed therein.

The cross-linked hydrophobic polymer when used herein is in an amount of from about 0.1% to about 10% by weight. The active ingredient can be one or more or a mixture of skin compatible oils, skin compatible humectants, emollients, moisturising agents, anti-acne actives and sunscreens. The polymer material is in the form of a powder, the powder being a combined system of particles. The system of powder particles forms a lattice which includes unit particles of less than about one micron in average diameter, agglomerates of fused unit particles of sized in the range of about 20 to 100 microns in average diameter and aggregates of clusters of fused agglomerates of sizes in the range of about 200 to 1,200 microns in average diameter.

The powder material of the present invention which can be employed as the carrier for the active ingredient can be broadly described as a cross-linked "post absorbed" hydrophobic polymer lattice. The powder preferably has entrapped and dispersed therein, an active which may be in the form of a solid, liquid or gas. The lattice is in particulate form and constitutes free flowing discrete solid particles when loaded with the active material. The lattice may contain a predetermined quantity of the active material. The polymer has the structural formula:

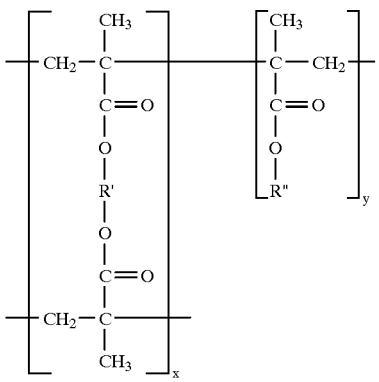

where the ratio of x to y is 80:20, R' is —CH$_2$CH$_2$— and R" is —(CH$_2$)$_{11}$CH$_3$.

The hydrophobic polymer is a highly cross-linked polymer, more particularly a highly cross-linked polymethacrylate copolymer. The material is manufactured by the Dow Coming Corporation, Midland, Mich., USA, and sold under the trademark POLYTRAP (RTM). It is an ultralight free-flowing white powder and the particles are capable of absorbing high levels of lipophilic liquids and some hydrophilic liquids while at the same time maintaining a free-flowing powder character. The powder structure consists of a lattice of unit particles less than one micron that are fused into agglomerates of 20 to 100 microns and the agglomerates are loosely clustered into macro-particles or aggregates of about 200 to about 1200 micron size. The polymer powder is capable of containing as much as four times its weight of fluids, emulsions, dispersions or melted solids.

Adsorption of actives onto the polymer powder can be accomplished using a stainless steel mixing bowl and a spoon, wherein the active is added to the powder and the spoon is used to gently fold the active into the polymer powder. Low viscosity fluids may be adsorbed by addition of the fluids to a sealable vessel containing the polymer and then tumbling the materials until a consistency is achieved. More elaborate blending equipment such as ribbon or twin cone blenders can also be employed.

Also suitable as a highly cross-linked polymethacrylate copolymer is Microsponges 5647. This takes the form of generally spherical particles of cross-linked hydrophobic polymer having a pore size of from about 0.01 μm to about 0.05 μm and a surface area of 200–300m$^2$/g. Again, it can be loaded with an active ingredient such as those described herein above. Preferred for use herein, however, is unloaded Microsponges 5640.

Other optional ingredients which can be included in the composition of the invention include preservatives in amounts generally less than about 1% by weight. Suitable preservatives include methylparaben, propylparaben, imidazolidimyl urea, phenoxyethanol, and mixtures thereof. The compositions may also contain fragrances, sunscreens and chelating agents.

Other optional ingredients which can be included in the compositions herein are sunscreens, vitamins and moisturising agents. In addition, cetrimonium bromide can be used as an anti-bacterial.

The powder make-up compositions of the present invention can be in the form of loose or pressed powder. The compositions can also be in the form of eyeshadow and blushers. Examples I–V

|  | I/% | II/% | III/% | IV/% | V/% |
|---|---|---|---|---|---|
|  | 6.00 | 0.00 | 3.00 | 12.0 | 2.00 |
| Cosmetic Mica | 0.00 | 10.0 | 0.00 | 0.00 | 5.00 |
| Zinc Oxide | 4.00 | 8.00 | 6.00 | 3.00 | 5.00 |
| Polyethylene B-12 | 7.00 | 2.00 | 10.0 | 1.00 | 5.00 |
| Zinc Stearate | 0.00 | 6.50 | 0.00 | 5.00 | 3.00 |
| Kaolin | 3.00 | 2.00 | 4.00 | 2.50 | 4.50 |
| Polytrap 6603 | 3.00 | 1.00 | 4.00 | 1.50 | 2.00 |
| Methyl paraben | 0.20 | 0.20 | 0.20 | 0.20 | 0.20 |
| Propyl paraben | 0.10 | 0.10 | 0.10 | 0.10 | 0.10 |
| Disodium EDTA | 0.05 | 0.05 | 0.00 | 0.00 | 0.05 |
| Salicylic acid | 2.00 | 2.00 | 1.50 | 1.00 | 1.00 |
| Red Iron Oxide | 0.60 | 0.50 | 0.70 | 0.90 | 0.50 |
| Yellow Iron Oxide | 0.70 | 0.40 | 0.80 | 0.90 | 0.50 |
| Black Iron Oxide | 0.20 | 0.20 | 0.30 | 0.30 | 0.20 |
| Permethyl 102A | 4.00 | 2.00 | 3.50 | 1.00 | 2.70 |
| DC 2502 | 2.50 | 4.00 | 3.00 | 4.50 | 4.00 |
| Talc |  |  | to 100 |  |  |

The powder cosmetic compositions of the above examples provide improved skin adhesion, wear, coverage and reduced rub-off characteristics.

The above compositions can be prepared as follows. The dry ingredients are weighed into a ribbon blender and mixed for about 15 minutes until homogeneous. Next the dry mixture is pulverised through an 020 herringbone screen. The liquid ingredients are then sprayed into the dry mixture with stirring. The batch is pulverised and sieved before being ready for packaging.

We claim:
1. A cosmetic composition comprising:
    (a) from about 0.1% to about 20% by weight of a branched chain aliphatic hydrocarbon selected from the group consisting of isododecane, isollexadecane, isoeicosane, isooctahexacontane, isohexapentacontahectane, isopentacontaoctactane, and mixtures thereof;
    (b) from about 0.1% to about 15% by weight of particulate polyethylene;
    (c) from about 0.1% to about 10% by weight of cross-linked hydrophobic acrylate or methacrylate copolymer;
    (d) from about 0.01% to about 20% of a silicone or a mixture of silicones, the silicone or mixture of silicones comprising an alkyl metliyisiloxane polymer having the formula:

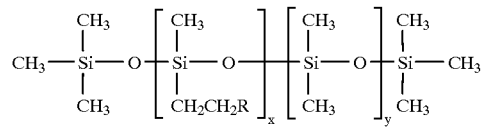

wherein x has a value of from the group consisting of about 1 to about 1000, y has a value of from 0 to about 1000 and R is selected from H and C$_1$–C$_{50}$ alkyl;
    the remainder of the composition comprising one or more cosmetic powder base components selected from the group consisting of pigments, matte finishing agents, fillers and binders, and mixture thereof; wherein said composition is in the form of a powder.

2. A cosmetic composition according to claim 1 wherein the branched chain aliphatic hydrocarbon is isoeicosane.

3. A cosmetic composition according to claim 1 comprising from about 0.5% to about 10% by weight of the branched chain aliphatic hydrocarbon.

4. A cosmetic composition according to claim 1 comprising from about 1% to about 10% by weight of the particulate polyethylene.

5. A cosmetic composition according to claim 1 additionally comprising an anti-acne active.

6. A cosmetic composition according to claim 5 wherein the anti-acne active is selected from the group consisting of salicylic acid, retinoic acid, azelaic acid, lactic acid, glycolic acid, pyruvic acid, flavonoids, and mixtures thereof.

7. A cosmetic composition according to claim 6 wherein the anti-acne active is salicylic acid.

8. A cosmetic composition according to claim 1 wherein the cross-linked hydrophobic copolymer is in the form of a lattice and wherein at least one active ingredient is dispersed uniformly throughout and entrapped within the copolymer lattice, the active ingredient being selected from the group consisting of skin compatible oils, skin compatible humectants, emollients, moisturising agents, anti-acne actives and sunscreens.

9. A cosmetic composition according to claim 1 additionally comprising from 0.01% to about 10% by weight of zinc oxide.

10. A cosmetic composition according to claim 9 wherein the zinc oxide has an average particle size of from about 0.1 $\mu$m to about 5 $\mu$m.

11. A cosmetic composition according to claim 9 wherein the zinc oxide has an average particle size of from about 0.5 $\mu$m to about 1.5 $\mu$m.

12. A cosmetic composition according to claim 1 wherein the composition is in the form of a loose or pressed powder having an average particle size prior to compression of from about 1 $\mu$m to about 100 $\mu$m.

13. A cosmetic composition according to claim 1 wherein the composition is in the form of a loose or pressed powder having an average particle size prior to compression of from about 5 $\mu$m to about 60 $\mu$m.

* * * * *

UNITED STATES PATENT AND TRADEMARK OFFICE
CERTIFICATE OF CORRECTION

PATENT NO. : 5,919,467
DATED : July 6, 1999
INVENTOR(S) : D. M. Jenkins et al..

It is certified that error appears in the above-identified patent and that said Letters Patent is hereby corrected as shown below:

In Col. 2, line 60, "Coming" should read --Corning--.

In Col. 5, line 23, "Coming" should read --Corning--.

In Col. 6, line 33, "isollexadecane" should read --isohexadecane--.

In Col. 6, line 61, "mixture" should read --mixtures--.

Signed and Sealed this

Eighth Day of May, 2001

*Attest:*

NICHOLAS P. GODICI

*Attesting Officer*     Acting Director of the United States Patent and Trademark Office